United States Patent [19]
Highsmith et al.

[11] Patent Number: 5,498,711
[45] Date of Patent: Mar. 12, 1996

[54] SYNTHESIS OF 4,10-DINITRO-2,6,8,12-TETRAOXA-4,10-DIAZATETRACYCLO[5.5.0.0⁵,⁹0³,¹¹]-DODECANE

[75] Inventors: Thomas K. Highsmith, North Ogden; W. Wayne Edwards, Tremonton; Robert B. Wardle, Logan, all of Utah

[73] Assignee: Thiokol Corporation, Ogden, Utah

[21] Appl. No.: 101,458

[22] Filed: Aug. 2, 1993

Related U.S. Application Data

[63] Continuation-in-part of Ser. No. 13,034, Feb. 3, 1993.
[51] Int. Cl.$^6$ ............................................ C07D 498/22
[52] U.S. Cl. ............................................ 540/546
[58] Field of Search ................................. 540/546

[56] References Cited

U.S. PATENT DOCUMENTS

| | | | |
|---|---|---|---|
| 3,365,454 | 1/1968 | Ferguson | 260/268 |
| 3,369,020 | 2/1968 | Ferguson | 260/268 |
| 4,487,938 | 12/1984 | Boileau et al. | 548/304 |

OTHER PUBLICATIONS

*Concise Chemical and Technical Dictionary*, 4th edition, H. Bennett, editor, (1986), p. 72.

Currie et al., "Base-catalysed Reactions of Glyoxal. Part I. 1,4-Diformyl- and 1,4-Bismethylsulphonyl-Derivatives of 2,3,5,6-tetrahydroxypiperazines", *J. Chem. Soc.*, (C), 1967, pp. 491-497.

"Methylsulfonylpiperazines", *Chemical Abstracts*, vol. 67, p. 3102, 1967, Imperial Chemical Industries Ltd.

Ramakrishnan et al., "4,10-Dinitro-2,6,8,12-Tetraoxa-4, 10-Diazatetracyclo[5.5.0.0$^{5,9}$0$^{3,11}$]Dodecane", *Heterocycles*, vol. 31, No. 3, pp. 479-480, 1990.

*Primary Examiner*—Philip I. Datlow
*Attorney, Agent, or Firm*—Ronald L. Lyons; Madson & Metcalf

[57] ABSTRACT

4,10-dinitro-2,6,8,12-tetraoxa-4,10-diazatetracyclo-[5.5.0.0$^{5,9}$0$^{3,11}$]dodecane is synthesized by reacting a diacyl-2,3,5,6-tetraoxypiperazine or tetraoxadiazaisowurtzitane derivative, a strong acid, and a nitrate source, such that an exothermic reaction occurs which proceeds at a temperature above ambient temperature. The reaction product is precipitated by cooling. It may be purified by washing with methanol and/or sodium bicarbonate and by simmering in nitric acid.

43 Claims, No Drawings

SYNTHESIS OF 4,10-DINITRO-2,6,8,12-TETRAOXA-4,10-DIAZATETRACYCLO[ 5.5.0.05,903,11] DODECANE

This invention is a continuation-in-part of U.S. patent application Ser. No. 08/013,034, filed Feb. 3, 1993 allowed, titled "Insensitive High Performance Explosive Compositions," which is incorporated herein by reference.

BACKGROUND OF THE INVENTION

1. Field of the Invention

This invention relates to the preparation of 4,10-dinitro-2,6,8,12-tetraoxa-4,10-diazatetracyclo[5.5.0.0$^{5,9}$0$^{3,11}$]dodecane. More specifically, the present invention relates to improved processes for synthesizing the stated compound.

2. Technology Background 4,10-dinitro-2,6,8,12-tetraoxa-4,10-diazatetracyclo [5.5.0.0$^{5,9}$0$^{3,11}$]dodecane has been prepared by a procedure reported by Joseph H. Boyer and colleagues in *Heterocycles*, vol. 31, no. 3, pp. 479–480 (1990). According to the reported procedure, 1,4-diformyl-2,3,5,6-tetrahydroxypiperazine (1) in trimeric glyoxal (dihydrate) was added to concentrated sulfuric acid at 0° C. and stirred at 10° C. to 15° C. for 5 hours. The reaction mixture was cooled to 0° C., and 100% nitric acid was added dropwise. Stirring was resumed for 2 hours at 0° to 10° C. and then for 45 hours at 25° C. The mixture was poured onto ice, and a colorless solid precipitated. It was isolated and washed to give a mixture which contains some 4,10-dinitro-2,6,8,12-tetraoxa-4,10-diazatetracyclo[5.5.0.0$^{5,9}$0$^{3,11}$]dodecane (2) (herein referred to as TEX). The reaction is shown below:

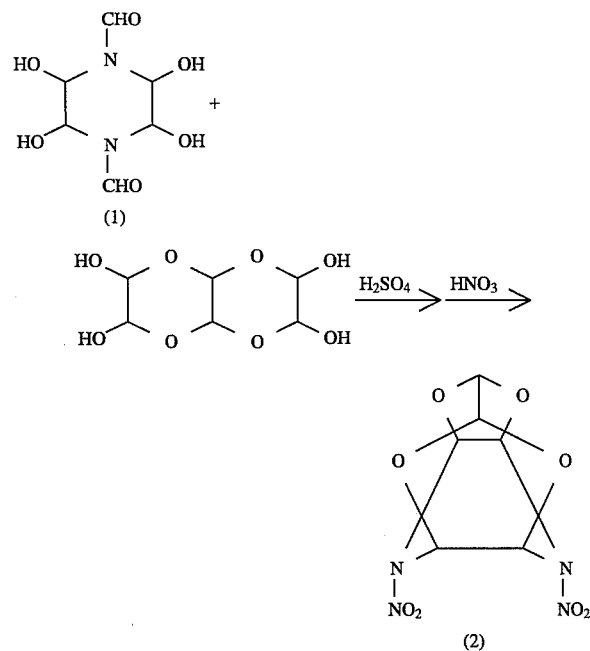

There are several disadvantages of the reported procedure for manufacturing TEX. For instance, the applicants have found that the reported procedure produces very impure TEX in low yields such that the described process is not capable of producing large quantities of TEX. The applicants have also found that glyoxal trimer is not necessary to produce TEX. Moreover, the reported procedure is very time-consuming, requiring over two days (approximately 52 hours) to complete. Finally, the reported procedure requires special reactants, such as pure nitric acid (100%), which are difficult to obtain and highly unstable.

It will be appreciated that there is a need in the art for alternative processes of manufacturing TEX which are efficient, produce TEX in high yield, and do not require the long processing time reported in the prior art (52 hours). It would also be an important advancement to provide processes for manufacturing TEX which utilize readily available reactants.

Such processes for manufacturing TEX are disclosed and claimed herein.

SUMMARY OF THE INVENTION

The invention relates to improved processes for manufacturing TEX. TEX may be prepared by reacting 1,4-diformyl-2,3,5,6-tetrahydroxypiperazine and derivatives thereof, with a strong acid and a nitrate source at temperatures greater than ambient temperature, and preferably in the range from about 50° C. to about 70° C. The reaction is exothermic and is complete within two to three hours. The reaction product is precipitated in a conventional manner, preferably by pouring onto ice, and purified to yield TEX. Purification may be accomplished by heating the reaction product in nitric acid, washing with methanol, and/or washing with a base to neutralize excess acid. The pure product may be obtained by recrystallization according to standard procedures. TEX is a useful explosive ingredient for high performance, low sensitivity explosive applications.

DETAILED DESCRIPTION OF THE INVENTION

The present invention is directed to improved processes for manufacturing TEX. TEX is obtained by reacting suitable hexa-substituted piperazine derivatives with a strong acid and a nitrate source at temperatures greater than ambient temperature, and preferably in the range from about 50° C. to about 70° C. The reaction is exothermic and is complete within two to three hours.

Suitable hexa-substituted piperazine derivatives have the following general formula:

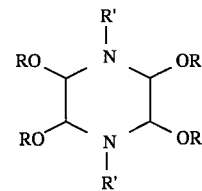

Where —OR is a good leaving group and R is H, R", —COR", —COOR", —SO$_3$R", —NO, —NO$_2$, acetal (including aliphatic, cycloaliphatic, and branched acetals), and cycloacetal; R' is a nitrolysable group such as —COR", —SO$_2$R", —NO$_2$, —NO, —COOR", t-butyl, cyclohexyl, and isopropyl; R" is H, C$_1$ to C$_{10}$ alkyl, branched alkyl, cyclo alkyl, and phenyl, substituted phenyl, and monocyclic heterocyclic compounds. As used herein, phenyl substituents include, but are not limited to, lower alkyl, branched alkyl, halogen, nitro, amino, substituted amino, alkoxy, acyl, and carbonyl containing moieties such as carboxyl, ester, ketone, etc. The monocyclic heterocyclic compounds used herein include heteroatoms selected from nitrogen, sulfur, and oxygen.

The hexa-substituted piperazine derivatives used to prepare TEX according to the present invention are preferably diacyltetraoxypiperazine derivatives. The following are examples of possible hexa-substituted piperazine derivatives which can be used in the process of the present invention:

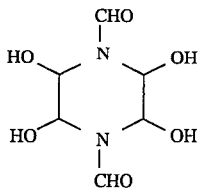

1,4-diformyl-2,3,5,6-tetrahydroxypiperazine

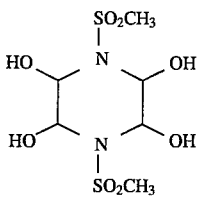

1,4-bis(methylsulphonyl)-2,3,5,6-tetrahydroxypiperazine

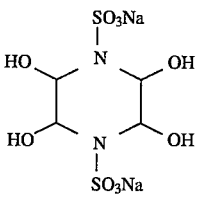

disodium 2,3,5,6-tetrahydroxypiperazine-1,4-disulphonate

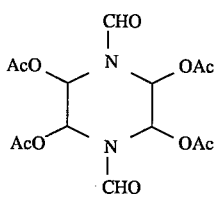

1,4-diformyl-2,3,5,6-tetraacetoxypiperazine

Typical hexa-substituted piperazine derivatives which may be used to synthesize TEX are prepared by reacting glyoxal with an amide, sulfonamide, or sulfonate salt. Other possible hexa-substituted piperazine derivatives which may be used in the present invention are reported in Currie, A. C., et al., "Base-catalysed Reactions of Glyoxal. Part I. 1,4-Diformyl- and 1,4-Bismethylsulphonyl-Derivatives of 2,3,5,6-tetrahydroxypiperazines," *Journal of the Chemical Society (Sect. C)*, pp. 491–496 (1967) and Dinwoodie, A. H., et al., "Base-catalysed Reactions of Glyoxal. Part II. 2,3,5,6-Tetrahydroxypiperazine- 1,4-disulphonic Acid Derivatives," *Journal of the Chemical Society (Sect. C)*, pp. 496–497 (1967).

As used herein, diacyltetraoxypiperazine derivatives also include TEX intermediate products, such as the tetraoxadiazaisowurtzitane derivatives shown below, because the tetraoxadiazaisowurtzitane derivatives may be prepared from diacyltetraoxypiperazine derivatives. TEX is prepared from the tetraoxadiazaisowurtzitane derivatives by nitrolysis of the N-acyl group.

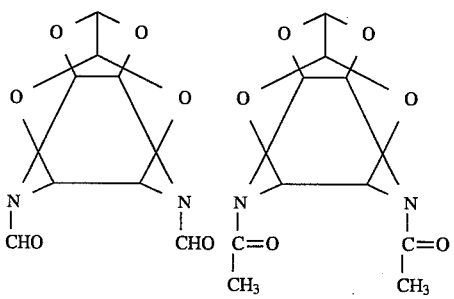

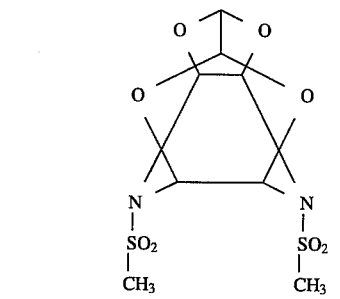

While not being bound by theory, it is believed the strong acid serves to catalyze the isowurtzitane structure formation. It is also believed the strong acid helps create nitronium ions from the nitrate source necessary to nitrate the TEX.

Typical strong acids which may be used in the process of the present invention include sulfuric acid, trifluoroacetic acid (TFA), trifluoroacetic anhydride (TFAA), and HCl. Nitrate sources which have been used successfully in the present invention include nitric acid and ammonium nitrate. Importantly, commercially available 70% or 90% nitric acid may be used in the present invention instead of 100% nitric acid required in the literature preparation.

The currently preferred strong acid and nitrate source is an acid mixture of nitric acid and sulfuric acid. This acid mixture may contain up to 60% concentrated $H_2SO_4$, by volume. The presently preferred ratio of concentrated nitric acid (90%, 1.52 gm/ml) to concentrated sulfuric acid is 60:40, by volume. It has been found that nitric acid (90% and 100% nitric acid) can serve as both the strong acid and nitrate source in the process of preparing TEX according to the present invention. The amount of acid mixture required to prepare TEX ranges from about 2:1 to about 5:1 milliliters acid mixture per gram substrate, and preferably is about 4:1. When ammonium nitrate is the nitrate source, from two to ten equivalents of ammonium nitrate are used for each equivalent of substrate.

The reaction product is precipitated, preferably by pouring onto ice, filtered, and purified to yield TEX. Currently preferred purification techniques include heating the reaction product in nitric acid, washing with methanol, and/or washing with a base to neutralize excess acid.

The pure product may be obtained by crystallization according to standard crystallization techniques. Typical crystallization solvents which may be used include acetonitrile, acetone, butyrolactone, nitric acid, ethyl acetate, pyridine, DMSO, and DMF.

During the synthesis of TEX, nitric acid is reduced and produces $NO_2$. Other nitrate sources, such as ammonium nitrate, also produce $NO_2$ during nitrolysis. If the reaction temperature becomes too high, $NO_2$ is rapidly released, causing the reaction mixture to undergo an uncontrolled exotherm. It has been found that urea added to the reaction mixture scavenges $NO_2$, inhibits foaming, and diminishes the likelihood of uncontrolled exotherm. Thus, urea is a preferred additive to the TEX reaction mixture. Typically, at least 0.5 equivalents urea (based upon the amount of diacyltetraoxypiperazine derivatives) is needed to be effective. It is currently preferred to include about 1 equivalent of urea in the reaction mixture. Those skilled in the art will appreciate that a significant excess amount of urea can be used, it is not preferred because it can lead to byproduct formation and can complicate purification.

As described more fully in the related application Ser. No. 08/013,034, filed Feb. 3, 1993, titled "Insensitive High Performance Explosive Compositions," TEX may be used either alone or in combination with conventional or novel solid explosive ingredients as the basis for formulating very high performance insensitive explosive compositions. For example, TEX may be used in combination with a binder, metal, and oxidizer to prepare low cost, castable explosives. TEX and a small amount of binder may also be used to prepare high solids (>90% TEX) pressable or extrudable explosives. Melt cast explosives may be prepared by combining TEX with an energetic or inert material having a relatively low melt temperature (<120° C.). These melt cast explosives may also contain a metal, oxidizer and other nitramine. TEX may also be used as the primary solid in simple castable or plastic formulations (up to 90% solids) using energetic or inert polymeric binders. This class of explosives may contain another nitramine (i.e., RDX, HMX), but will not normally contain an oxidizer or metal.

The following examples are offered to further illustrate the synthesis methods of the present invention. These examples are intended to be purely exemplary and should not be viewed as a limitation on any claimed embodiment.

Example 1

Literature Preparation of TEX

A mixture of 4.0 g (20 mmol) 2,3,5,6-Tetrahydroxy-1,4-diformylpiperazine (THDFP) and glyoxal trimer, 2.1 g (10 mmol) was added to a stirred solution of concentrated sulfuric acid, 25 ml, while maintaining the temperature at 0° C. with an ice water bath. Following the addition the bath was removed and the temperature was allowed to rise to 15° C. After five hours at this temperature the reaction mixture was again cooled to 0° C. by reapplication of the ice water bath. Freshly distilled 100% $HNO_3$, 25 ml (prepared from 90% $HNO_3$ and $H_2SO_4$) was added dropwise. Stirring was continued for 2 hours at 0° C. then 48 hours at room temperature. The mixture was then poured on ice and the solid precipitate collected by filtration, washed with water and then ethanol several times. After drying under vacuum at 60° C. the weight of the solid was 3.3 g. Subsequent analysis of this material by $^1H$ NMR indicated that the product was predominantly unchanged glyoxal trimer containing only a small amount of TEX (<20%). Repeated digestions and recrystallizations from ethyl acetate and acetonitrile provided an analytical sample which displayed the proton and carbon NMR resonances as well as FTIR absorbances reported by Joseph H. Boyer and colleagues in *Heterocycles*, vol. 31, pp. 479–80 (1990).

Example 2

Preparation of TEX

To a water cooled, vigorously stirred solution of 390 ml of white fuming nitric acid and 250 ml of concentrated sulfuric acid in a 4 liter erlenmeyer flask was added a mixture of 206 g (1.0 mole) of THDFP and 33 g (0.55 mole) urea, portionwise such that the temperature did not exceed 50° C. Following the addition the water bath was removed and the temperature was allowed to rise to 65° C. The temperature gradually fell to approximately 30° C. over one half hour, following which the entire contents of the flask were poured on ice and the solid precipitate collected on a glass frit.

The solid was then washed thoroughly with water, saturated sodium bicarbonate, water again, and finally methanol. The crude product was then dried in vacuo at 60° C. overnight, furnishing 108.8 g of a pale yellow solid which when analyzed by $^1H$ NMR indicated a purity of 97% (3% mono-formyl-mononitro). An analytical sample was prepared by several recrystallizations from acetonitrile which was indistinguishable from that described by Boyer et al. $^1H$ NMR (Varian 300 MHz)(DMSO d6); δ7.08 (s,4H), δ5.95(s, 2H); $^{13}C$ NMR (DMSO d6); δ102.65, δ82.63 IR: 1590, 1285, 1250, 1050, 900, 875 $CM^{-1}$ Anal. Calculated for C 27.4%, H 2.29%, N 21.3%; found: C 27.4%, H 2.24%, N 20.9%.

Examples 3–14

TEX was prepared based upon the procedure of Example 2, except that the procedure was carried out under a variety of different conditions and range of acids to produce TEX. Table 1 illustrates the breadth of parameters.

TABLE 1

| Example | THDFP (gm) | Acid (ml) | Acid Ratio* | Urea (gm) | Yield (gm) |
|---------|------------|-----------|-------------|-----------|------------|
| 3 | 50 | 101.1 | 61/40 | 0 | 37.1 |
| 4 | 200 | 500 | 3/2 | 33 | 65 |
| 5 | 100 | 850 | 1.5/7 | 33 | 16.2 |
| 6 | 200 | 500 | 3/2 | 66 | 48.6 |
| 7 | 206 | 500 | 3/2 | 100 | 36.0 |
| 8 | 206 | 650 | 2.5/4 | 33 | 63.0 |
| 9 | 206 | 640 | 2.5/3.9 | 66 | 70.0 |
| 10 | 200 | 500 | 3/2 | 0 | 48.4 |
| 11 | 100 | 500 | 1/1 | 0 | 31.4 |
| 12 | 100 | 400 | 2.5/1.5 | 0 | 20.0 |
| 13 | 100 | 300 | 1.8/1.2 | 0 | 9.3 |
| 14 | 100 | 400 | 3/1 | 0 | 24.0 |

*(v/v) 90% $HNO_3$/concentrated $H_2SO_4$

Example 15

Purification of Crude TEX with Nitric Acid

A suspension of 50.0 g of crude (any material with a purity of less than 99% by NMR) TEX in 200 ml of white fuming nitric acid was prepared in a 500 ml round bottom flask. The flask was fitted with a condenser and the contents heated to 80° C. with an oil bath for 8 hr. The yellow solution was then allowed to cool to room temperature and subsequently poured on ice. The solid was collected, washed with water, sodium bicarbonate and more water. The product was then dried in vacuo yielding 31.42 g of analytically pure (>99%) TEX.

Example 16

TEX from 1,4-bismethylsulfonyl-2,3,5,6-tetrahydroxypiperazine

To a solution of 24 ml of white fuming nitric acid and 16 ml of concentrated sulfuric acid was added 1,4-bismethylsulfonyl- 2,3,4,5-tetrahydroxypiperazine (prepared according to Currie, A. C. et al., *Journal of the Chemical Society (Sect. C).*, pp. 491–496, (1967)), 15.0 g (0.048 mole). After one half hour the reaction began to fume and the temperature rose to above 100° C. At this point the mixture was poured on ice and the solid collected. This material was then washed with water and air dried. The solid was then extracted with hot ethyl acetate leaving 5.5 g of unreacted starting material. The filtrate was evaporated in vacuo resulting in a pale yellow solid 600 mg composed predominately of TEX by $^1$H NMR.

Example 17

Preparation of 4,10-diformyl-2,6,8,12-tetraoxa-4,10-diazatetracyclo[5.0.0$^{5,9}$0$^{3,11}$]dodecane (DFIW)

In a 100 ml 3 neck round bottom flask equipped with a stir bar thermometer, argon inlet and outlet was placed 50 ml of trifluoroacetic anhydride. The flask was immersed in an ice bath and 9 ml (0.194 mole, 12.3 g) of freshly distilled 100% nitric acid added dropwise with stirring. After one half hour at 0° C. 10 g (48.5 mmole) of DFTHP was added in one portion. The reaction was allowed to stir overnight at room temperature after which 3 ml of water was added. The solid was then collected by filtration and subsequently washed with methanol twice, then ether twice. After air drying the white solid weighed 16.5 g. This material was recrystallized from acetone yielding pure DFIW melting sharply at 169° C. $^1$H NMR bs (CHO) δ8.75 (2H), bs+shoulder δ7.10,7.22 (6H); $^{13}$C NMR δ168.75 (CHO), δ85.12 (CH), δ78.89 (CH); IR; 1650, 1220, 935, 790 cm$^{-1}$.

Example 18

Preparation of TEX from DFIW

In a 50 ml round bottom flask equipped with a stir bar and argon inlet was placed 3 ml of white fuming nitric acid and 1.0 g (4.4 mmole) of DFIW prepared according to Example 17. The solution thus prepared was stirred overnight at room temperature. The reaction was then poured on ice and the solid precipitate collected, washed with water and dried in vacuo, yielding 0.23 g of TEX.

Example 19

Preparation of TEX from 1,4-diformyl-2,3,5,6-tetraacetoxypiperazine (TADFP)

In a 50 ml round bottom flask equipped with a stir bar and argon inlet was placed 25 ml of white fuming nitric acid and 20 drops of concentrated hydrochloric acid. To this solution was added TADFP (prepared according to Currie, A. C. et al., *Journal of the Chemical Society (Sect. C)*, pp. 491–496, (1967)) in one portion. The reaction gradually became clear and stirring was continued overnight at room temperature. After this time the reaction was poured on ice and the solid precipitate collected by filtration, washed thoroughly with water and dried yielding 500 mg of TEX as a pale yellow solid.

Example 20

Preparation of TEX from disodium-2,3,5,6-tetrahydroxypiperazine-1,4-disulfonate

In a dry 100 ml, single neck round bottom flask equipped with a stir bar and argon inlet was placed 1.0 g of solid SO$_3$ (12.5 mmole). The flask was then immersed in an ice bath and freshly distilled 100% nitric acid, 4.0 ml (96.5 mmole) was added dropwise via syringe. The suspension was stirred for one half hour by which time all the SO$_3$ had dissolved resulting in a pale yellow solution. The sulfonate salt 1.0 g (3.2 mmole) was then added in portions over 2–3 minutes. The cooling bath was then removed and stirring continued overnight. The reaction was then poured on ice and the solid collected by filtration. After drying the product was analyzed by $^1$H NMR and found to contain TEX heavily contaminated with reaction byproducts.

Example 21

Preparation of TEX from 70% Nitric Acid

In a one liter erlenmeyer flask containing a magnetic stir bar was placed 180 ml of 70% nitric acid. The flask was cooled in an ice bath and THDFP, 103 g (0.5 mole) was added in several portions. No temperature rise was observed during or following the addition and the suspension thus prepared was stirred overnight at room temperature. The mixture was then poured on ice and the solid collected by filtration. After air drying the solid was dissolved in a 2:1 mixture of ethyl acetate and methanol, and passed through a short pad of silica gel on a filter frit. The filtrate was allowed to stand for two days at which time the crystals which had deposited were collected and dried in vacuo, providing 8.3 g of pure TEX. Nitric acid of higher concentration may be substituted in this reaction but the yields under similar conditions are not substantially higher; e.g.: with 100% HNO$_3$, 1.0 g THDFP gave 200 mg of TEX and with 90% HNO$_3$, 50 g THDFP gave 12.0 g TEX.

Example 22

Preparation of TEX from Ammonium Nitrate and Sulfuric Acid

In a one liter erlenmeyer flask with a large stir bar was placed 750 ml of concentrated sulfuric acid. To the acid was added 240 g of oven dried ammonium nitrate in portions while maintaining the temperature below 50° C. To the resulting clear solution was added DFTHP, 206 g (1 mole) in two large portions. The thick reaction mixture was stirred at room temperature overnight. Another 160 g of ammonium nitrate was then added and the exothermic process was allowed to subside (about 4 hours) after which time the slurry was poured on ice and the solid collected by filtration. The solid was then washed with sodium bicarbonate, then water and air dried. The dried solid was then extracted with boiling ethyl acetate and after cooling two crops of impure TEX was collected totalling 46 g. One additional crystallization from ethyl acetate gave 20 g of clean TEX.

Example 23

Preparation of TEX via 4,10-diacetyl-2,6,8,12-tetraoxa-4,10-diazatetracyclo[5.0.0$^{5,9}$0$^{3,11}$]dodecane (DAIW)

In a 500 ml round bottom flask equipped with a stir bar and thermometer was placed 100 ml of 40% glyoxal solution (0.69 mole) to which was added 46.6 ml (1.38 mole) of concentrated ammonium hydroxide solution. During the addition the temperature rose to 70° C. The resulting brown solution was stirred with cooling in an ice bath for two hours after which the water was removed in vacuo. Five grams of this amorphous brown tar was then treated with acetyl nitrate in acetic anhydride (prepared from 25 ml acetic anhydride and 4 ml 100% HNO₃ at 0° C.). Following an aqueous work up the product, DAIW, 2.60 g, was obtained as a pale yellow oil which slowly crystallized. One half gram of this material was then treated with 2 ml of 100% $HNO_3$ at 40° C. for 2 hours. The mixture was then poured on ice and the solid precipitate collected by filtration. After thoroughly washing with water, the solid was dried in vacuo providing 80 mg of TEX as a pale yellow solid.

Example 24

Preparation of TEX from fuming sulfuric acid

In a 250 ml round bottom flask equipped with a stir bar, thermometer, and argon inlet was placed a mixture of 20 ml 25% oleum and 54.5 ml white fuming nitric acid. A mixture of DFTHP, 51.5 g (250 mmole) and urea, 15 g (250 mmole) was then added portionwise over 20 minutes. The temperature during this addition was 52° C., following the addition the temperature increased to 65° C. over 11 minutes. After another one half hour the temperature had dropped to 28° C., at which time the whole contents were poured on ice. The solid was then collected by filtration, washed sequentially with water, saturated sodium bicarbonate, more water and finally air dried. TEX was obtained as pale yellow solid, 10.5 g.

From the foregoing it will be appreciated that the present invention provides alternative processes for manufacturing TEX which are efficient, produce TEX in high yield, and are rapid. The present invention also provides processes for manufacturing TEX which utilize readily available reactants.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A process for preparing 4,10-dinitro-2,6,8,12-tetraoxa-4,10-diazatetracyclo-[5.5.0.0$^{5,9}$0$^{3,11}$]dodecane comprising the steps of:

(a) reacting a mixture of a hexa-substituted piperazine derivative, a strong acid, and a nitrate source, such that an exothermic reaction occurs which proceeds at a reaction temperature substantially above ambient temperature, said hexa-substituted piperazine derivative having the following structure:

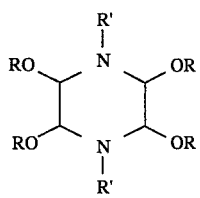

Where —OR is a good leaving group and R is H, R", —COR", —COOR", —SO₃R", —NO, —NO₂, acetal (including aliphatic, cycloaliphatic, or branched acetals), or cycloacetal; R' is a nitrolysable group selected from —COR", —SO₂R", —SO₃M, —NO₂, —NO, —COOR", t-butyl, cyclohexyl, and isopropyl; M is an alkali metal; R" is H, C₁ to C₁₀ alkyl, branched alkyl, cycloalkyl or phenyl, substituted phenyl, or a monocyclic heterocyclic radical;

(b) precipitating a reaction product from the reaction mixture; and (c) purifying the reaction product.

2. A process for preparing 4,10-dinitro-2,6,8,12-tetraoxa-4,10-diazatetracyclo-[5.5.0.0$^{5,9}$0$^{3,11}$]dodecane as defined in claim 1, wherein the nitrate source is nitric acid.

3. A process for preparing 4,10-dinitro-2,6,8,12-tetraoxa-4,10-diazatetracyclo-[5.5.0.0$^{5,9}$0$^{3,11}$]dodecane as defined in claim 1, wherein the nitrate source is ammonium nitrate.

4. A process for preparing 4,10-dinitro-2,6,8,12-tetraoxa-4,10-diazatetracyclo-[5.5.0.0$^{5,9}$0$^{3,11}$]dodecane as defined in claim 1, wherein the strong acid is sulfuric acid.

5. A process for preparing 4,10-dinitro-2,6,8,12-tetraoxa-4,10-diazatetracyclo-[5.5.0.0$^{5,9}$0$^{3,11}$]dodecane as defined in claim 1, wherein the strong acid is selected from trifluoroacetic acid, nitric acid, trifluoroacetic anhydride, and HCl.

6. A process for preparing 4,10-dinitro-2,6,8,12-tetraoxa-4,10-diazatetracyclo-[5.5.0.0$^{5,9}$0$^{3,11}$]dodecane as defined in claim 1, wherein the reaction product is precipitated by cooling the reaction mixture.

7. A process for preparing 4,10-dinitro-2,6,8,12-tetraoxa-4,10-diazatetracyclo-[5.5.0.0$^{5,9}$0$^{3,11}$]dodecane as defined in claim 1, wherein the precipitated reaction product is purified by treating with sodium bicarbonate.

8. A process for preparing 4,10-dinitro-2,6,8,12-tetraoxa-4,10-diazatetracyclo-[5.5.0.0$^{5,9}$0$^{3,11}$]dodecane as defined in claim 1, wherein the reaction product is purified by washing with methanol.

9. A process for preparing 4,10-dinitro-2,6,8,12-tetraoxa-4,10-diazatetracyclo-[5.5.0.0$^{5,9}$0$^{3,11}$]dodecane as defined in claim 1, wherein the reaction product is purified by simmering in nitric acid.

10. A process for preparing 4,10-dinitro-2,6,8,12-tetraoxa-4,10-diazatetracyclo-[5.5.0.0$^{5,9}$0$^{3,11}$]dodecane as defined in claim 1, wherein the reaction temperature is maintained below about 70° C.

11. A process for preparing 4,10-dinitro-2,6,8,12-tetraoxa-4,10-diazatetracyclo-[5.5.0.0$^{5,9}$0$^{3,11}$]dodecane as defined in claim 1, wherein the hexa-substituted piperazine derivative is the following compound:

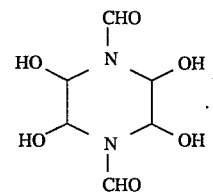

12. A process for preparing 4,10-dinitro-2,6,8,12-tetraoxa-4,10-diazatetracyclo-[5.5.0.0$^{5,9}$0$^{3,11}$]dodecane as defined in claim 1, wherein the hexa-substituted piperazine derivative is the following compound:

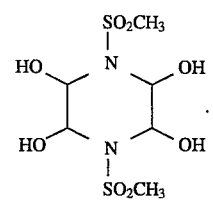

13. A process for preparing 4,10-dinitro-2,6,8,12-tetraoxa-4,10-diazatetracyclo-[5.5.0.0$^{5,9}$0$^{3,11}$]dodecane as defined in claim 1, wherein the hexa-substituted piperazine derivative is the following compound:

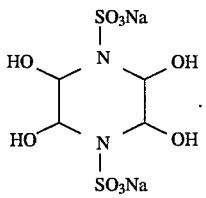

14. A process for preparing 4,10-dinitro-2,6,8,12-tetraoxa- 4,10-diazatetracyclo-[5.5.0.0$^{5,9}$0$^{3,11}$]dodecane as defined in claim 1, wherein the hexa-substituted piperazine derivative is the following compound:

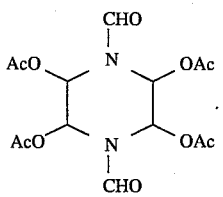

15. A process for preparing 4,10-dinitro-2,6,8,12-tetraoxa- 4,10-diazatetracyclo-[5.5.0.0$^{5,9}$0$^{3,11}$]dodecane as defined in claim 1, wherein the reaction mixture further comprises urea.

16. A process for preparing 4,10-dinitro-2,6,8,12-tetraoxa- 4,10-diazatetracyclo-[5.5.0.0$^{5,9}$0$^{3,11}$]dodecane as defined in claim 1, wherein the exothermic reaction occurs which proceeds at a reaction temperature above 50° C.

17. A process for preparing 4,10-dinitro-2,6,8,12-tetraoxa-4,10-diazatetracyclo-[5.5.0.0$^{5,9}$0$^{3,11}$]dodecane comprising the steps of:

(a) reacting a mixture of 1,4-diformyl-2,3,5,6 -tetrahydroxypiperazine, a strong acid, and a nitrate source, such that an exotherimic reaction occurs which proceeds at a reaction temperature substantially above ambient temperature and below about 70° C.;

(b) precipitating a reaction product from the reaction mixture; and (c) purifying the reaction product.

18. A process for preparing 4,10-dinitro-2,6,8,12-tetraoxa-4,10-diazatetracyclo-[5.5.0.0$^{5,9}$0$^{3,11}$]dodecane as defined in claim 17, wherein the nitrate source is nitric acid.

19. A process for preparing 4,10-dinitro-2,6,8,12-tetraoxa-4,10-diazatetracyclo-[5.5.0.0$^{5,9}$0$^{3,11}$]dodecane as defined in claim 18, wherein the strong acid is sulfuric acid.

20. A process for preparing 4,10-dinitro-2,6,8,12-tetraoxa-4,10-diazatetracyclo-[5.5.0.0$^{5,9}$0$^{3,11}$]dodecane as defined in claim 18, wherein the strong acid is selected from trifluoroacetic acid, nitric acid, trifluoroacetic anhydride, and HCl.

21. A process for preparing 4,10-dinitro-2,6,8,12-tetraoxa-4,10-diazatetracyclo-[5.5.0.0$^{5,9}$0$^{3,11}$]dodecane as defined in claim 17, wherein the nitrate source is ammonium nitrate.

22. A process for preparing 4,10-dinitro-2,6,8,12-tetraoxa-4,10-diazatetracyclo-[5.5.0.0$^{5,9}$0$^{3,11}$]dodecane as defined in claim 21, wherein the strong acid is sulfuric acid.

23. A process for preparing 4,10-dinitro-2,6,8,12-tetraoxa-4,10-diazatetracyclo-[5.5.0.0$^{5,9}$0$^{3,11}$]dodecane as defined in claim 21, wherein the strong acid is selected from trifluoroacetic acid, nitric acid, trifluoroacetic anhydride, and HCl.

24. A process for preparing 4,10-dinitro-2,6,8,12-tetraoxa-4,10-diazatetracyclo-[5.5.0.0$^{5,9}$0$^{3,11}$]dodecane as defined in claim 17, wherein the reaction product is precipitated by cooling the reaction mixture.

25. A process for preparing 4,10-dinitro-2,6,8,12-tetraoxa-4,10-diazatetracyclo-[5.5.0.0$^{5,9}$0$^{3,11}$]dodecane as defined in claim 17, wherein the precipitated reaction product is purified by treating with sodium bicarbonate.

26. A process for preparing 4,10-dinitro-2,6,8,12-tetraoxa-4,10-diazatetracyclo-[5.5.0.0$^{5,9}$0$^{3,11}$]dodecane as defined in claim 17, wherein the reaction product is purified by washing with methanol.

27. A process for preparing 4,10-dinitro-2,6,8,12-tetraoxa-4,10-diazatetracyclo-[5.5.0.0$^{5,9}$0$^{3,11}$]dodecane as defined in claim 17, wherein the reaction product is purified by simmering in nitric acid.

28. A process for preparing 4,10-dinitro-2,6,8,12-tetraoxa-4,10-diazatetracyclo-[5.5.0.0$^{5,9}$0$^{3,11}$]dodecane as defined in claim 17, wherein the reaction mixture further comprises urea.

29. A process for preparing 4,10-dinitro-2,6,8,12-tetraoxa- 4,10-diazatetracyclo-[5.5.0.0$^{5,9}$0$^{3,11}$]dodecane as defined in claim 17, wherein the exothermic reaction occurs which proceeds at a reaction temperature above 50° C.

30. A process for preparing 4,10-dinitro-2,6,8,12-tetraoxa-4,10-diazatetracyclo-[5.5.0.0$^{5,9}$0$^{3,11}$]dodecane comprising the steps of:

(a) reacting a mixture of a tetraoxadiazaisowurtzitane derivative, a strong acid, and a nitrate source, such that an exothermic reaction occurs which proceeds at a reaction temperature substantially above ambient temperature, said tetraoxadiazaisowurtzitane derivative having the following structure:

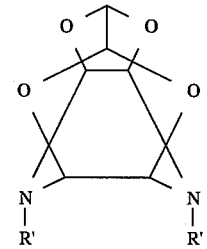

Where R' is a nitrolysable group selected from —COR", —SO$_2$R", —NO$_2$, —NO, —COOR", t-butyl, cyclohexyl, and isopropyl; R" is H, C$_1$ to C$_{10}$ alkyl, branched alkyl, cycloalkyl, or phenyl, substituted phenyl, or a monocyclic heterocyclic radical;

(b) precipitating a reaction product from the reaction mixture; and (c) purifying the reaction product.

31. A process for preparing 4,10-dinitro-2,6,8,12-tetraoxa-4,10-diazatetracyclo-[5.5.0.0$^{5,9}$0$^{3,11}$]dodecane as defined in claim 30, wherein the nitrate source is nitric acid.

32. A process for preparing 4,10-dinitro-2,6,8,12-tetraoxa-4,10-diazatetracyclo-[ 5.5.0.0$^{5,9}$0$^{3,11}$]dodecane as defined in claim 30, wherein the nitrate source is ammonium nitrate.

33. A process for preparing 4,10-dinitro-2,6,8,12-tetraoxa-4,10 -diazatetracyclo-[5.5.0.0$^{5,9}$0$^{3,11}$]dodecane as defined in claim 30, wherein the strong acid is sulfuric acid.

34. A process for preparing 4,10-dinitro-2,6,8,12-tetraoxa-4,10 -diazatetracyclo-[5.5.0.0$^{5,9}$0$^{3,11}$]dodecane as defined in claim 30, wherein the strong acid is selected from trifluoroacetic acid, nitric acid, trifluoroacetic anhydride, and HCl.

35. A process for preparing 4,10-dinitro-2,6,8,12-tetraoxa-4,10 -diazatetracyclo-[5.5.0.0$^{5,9}$0$^{3,11}$]dodecane as defined in claim 30, wherein the reaction product is precipitated by cooling the reaction mixture.

36. A process for preparing 4,10-dinitro-2,6,8,12-tetraoxa-4,10-diazatetracyclo-[5.5.0.0$^{5,9}$0$^{3,11}$]dodecane as defined in claim 30, wherein the precipitated reaction product is purified by treating with sodium bicarbonate.

37. A process for preparing 4,10-dinitro-2,6,8,12-tetraoxa-4,10-diazatetracyclo-[5.5.0.0$^{5,9}$0$^{3,11}$]dodecane as defined in claim 30, wherein the reaction product is purified by washing with methanol.

38. A process for preparing 4,10-dinitro-2,6,8,12-tetraoxa-4,10-diazatetracyclo-[5.5.0.0$^{5,9}$0$^{3,11}$]dodecane as defined in claim 30, wherein the reaction product is purified by simmering in nitric acid.

39. A process for preparing 4,10-dinitro-2,6,8,12-tetraoxa-4,10-diazatetracyclo-[5.5.0.0$^{5,9}$0$^{3,11}$]dodecane as defined in claim 30, wherein the reaction temperature is maintained below about 70° C.

40. A process for preparing 4,10-dinitro-2,6,8,12-tetraoxa-4,10-diazatetracyclo-[5.5.0.0$^{5,9}$0$^{3,11}$]dodecane as defined in claim 30, wherein the tetraoxadiazaisowurtzitane derivative is the following compound:

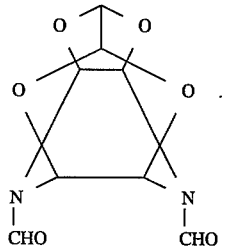

41. A process for preparing 4,10-dinitro-2,6,8,12-tetraoxa-4,10-diazatetracyclo-[5.5.0.0$^{5,9}$0$^{3,11}$]dodecane as defined in claim 30, wherein the tetraoxadiazaisowurtzitane derivative is the following compound:

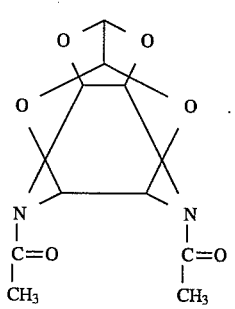

42. A process for preparing 4,10-dinitro-2,6,8,12-tetraoxa-4,10-diazatetracyclo-[5.5.0.0$^{5,9}$0$^{3,11}$]dodecane as defined in claim 30, wherein the tetraoxadiazaisowurtzitane derivative is the following compound:

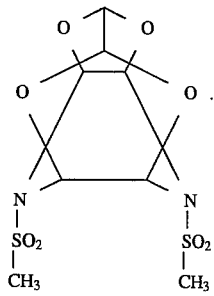

43. A process for preparing 4,10-dinitro-2,6,8,12-tetraoxa-4,10-diazatetracyclo-[5.5.0.0$^{5,9}$0$^{3,11}$]dodecane as defined in claim 30, wherein the exothermic reaction occurs which proceeds at a reaction temperature above 50° C.

* * * * *